US012714667B2

(12) United States Patent
Nam et al.

(10) Patent No.: US 12,714,667 B2
(45) Date of Patent: Aug. 25, 2026

(54) LIQUID PREPARATION OF L-SERINE OR PHARMACEUTICALLY ACCEPTABLE SALT THEREOF AND METHOD FOR PREPARING SAME

(71) Applicant: ASTROGEN, INC., Daegu (KR)

(72) Inventors: Hee-Sook Nam, Seoul (KR); Soyoung Kwak, Daegu (KR); Sun-Ha Cheon, Daegu (KR); Su-Kyeong Hwang, Daegu (KR); Hyung Chul Ryu, Hwaseong-si (KR)

(73) Assignee: ASTROGEN, INC., Daegu (KR)

( * ) Notice: Subject to any disclaimer, the term of this patent is extended or adjusted under 35 U.S.C. 154(b) by 275 days.

(21) Appl. No.: 18/282,675

(22) PCT Filed: Mar. 17, 2022

(86) PCT No.: PCT/KR2022/003789

§ 371 (c)(1),
(2) Date: Sep. 18, 2023

(87) PCT Pub. No.: WO2022/197140

PCT Pub. Date: Sep. 22, 2022

(65) Prior Publication Data

US 2024/0173253 A1 May 30, 2024

(30) Foreign Application Priority Data

Mar. 19, 2021 (KR) ........................ 10-2021-0035796

(51) Int. Cl.

| | |
|---|---|
| ***A61K 9/00*** | (2006.01) |
| ***A61K 31/198*** | (2006.01) |
| ***A61K 47/12*** | (2006.01) |
| ***A61K 47/32*** | (2006.01) |
| ***A61K 47/38*** | (2006.01) |

(52) U.S. Cl.

CPC .......... *A61K 9/0095* (2013.01); *A61K 31/198* (2013.01); *A61K 47/12* (2013.01); *A61K 47/32* (2013.01); *A61K 47/38* (2013.01)

(58) Field of Classification Search

None

See application file for complete search history.

(56) References Cited

U.S. PATENT DOCUMENTS

| | | | | |
|---|---|---|---|---|
| 9,539,226 | B2 | 1/2017 | Lee et al. | |
| 10,052,297 | B2 * | 8/2018 | Dechelette | A61K 8/345 |
| 2004/0192615 | A1 | 9/2004 | Hageman | |
| 2019/0046486 | A1 | 2/2019 | De Rienzo et al. | |

FOREIGN PATENT DOCUMENTS

| | | | | |
|---|---|---|---|---|
| CN | 106562143 | A | 4/2017 | |
| CN | 107334008 | A | 11/2017 | |
| EP | 1 108 429 | A2 | 6/2001 | |
| JP | 4-1130 | A | 1/1992 | |
| KR | 10-2012-0008125 | A | 1/2012 | |
| KR | 10-2012-0089231 | A | 8/2012 | |
| KR | 10-1672347 | B1 | 11/2016 | |
| KR | 10-2091620 | B1 | 3/2020 | |
| WO | WO-2011000930 | A1 * | 1/2011 | A61P 43/00 |

OTHER PUBLICATIONS

Lukic et al. (Toward Optimal pH of the Skin and Topical Formulations: From the Current State of the Art to Tailored Products, Cosmetics 2021, 8(3), 69). (Year: 2021).*

Chang et al. (Generic Development of Topical Dermatologic Products; Formulation Development, Process Development, and Testing of Topical Dermatologic Products, The AAPS Journal, vol. 35, No. 1, Jan. 2013). (Year: 2013).*

Oral Liquid Pharmaceutical Dosage Forms, (Pharmaguideline, accessed online Nov. 7, 2025, Wayback Machine Archive Availability dated Mar. 28, 2013). (Year: 2013).*

Introduction to Sweeteners in Nutraceuticals, (All4Nutra, accessed online Nov. 7, 2025, Wayback Machine Archive availability of Feb. 15, 2018). (Year: 2018).*

Extended European Search Report dated Apr. 8, 2025 from the European Patent Office in Application No. 22771806.1.

Amazon, "Absonutrix L-Serine Complex 500 mg" Online Web page, https://www.amazon.com/dp/B0819C1WJZ?ref=cm_sw_r_cp_ud_dp_QM3FX67FMTG64C351WJH&ref_=cm_sw_r_cp_ud_dp_QM3FX67FMTG64C351WJH&social_share=cm_sw_r_cp_ud_dp_QM3FX67FMTG64C351WJH, available as of Nov. 10, 2019 (7 pages).

Iman Aldahhan, Lecture "Pharmaceutical Technology 3rd stage: Syrups" University of Mustansiriyah, Oct. 18, 2018, (14 pages) https://uomustansiriyah.edu.iq/media/lectures/4/4_2018_10_18!06_01_01_PM.pdf.

"L-Serine", Chemical Book, 2017, Retrieved from URL: "https://web.archive.org/web/20170712190157/https://www.chemicalbook.com/ChemicalProductProperty_ JP_CB5673304.htm", pp. 2-4 (3 pages total).

Moon-Hee Kim et al., Effects of Sample Pretreatment in Amino Acid Analysis, Korean journal of clinical pathology, 2001; pp. 34-39, 21(1).

Anonymous, "L-SERINE", Online web page, https://www.alzdiscovery.org/cognitive-vitality/ratings/l-serine, last visited May 22, 2018, pp. 4.

International Search Report for PCT/KR2022/003789 dated Jun. 30, 2022.

Mintel GNDP, "L-Amino and Short Peptides, XXI Power Liquid Amino", ART Sovremennye Nauchnye, Russia, Sep. 2016, Record ID: 4055953, pp. 1-5 (5 pages total).

Mintel GNDP, "Liquid Multi-Vitamin Dietary Supplement Packet", Healthworks, USA, Oct. 2003, Record ID: 10151253, pp. 1-3 (3 pages total).

* cited by examiner

*Primary Examiner* — Melissa S Mercier

(74) *Attorney, Agent, or Firm* — Sughrue Mion, PLLC

(57) ABSTRACT

A liquid preparation and a method for preparing the liquid preparation are disclosed. The liquid preparation contains a high-concentration L-serine or a pharmaceutically acceptable salt thereof, and shows an excellent stability and safety. The liquid preparation exhibits excellent pharmacological effects and is suitable for preventing or treating a central nervous system disease.

24 Claims, 1 Drawing Sheet

【Fig. 1】
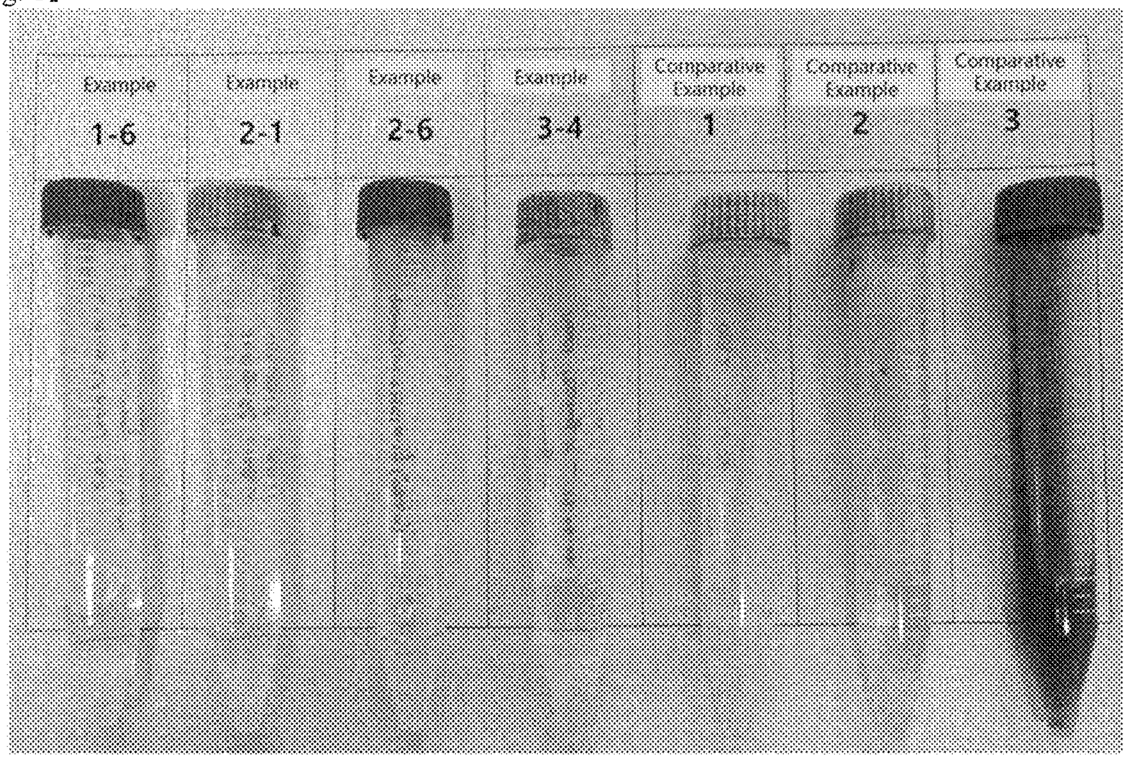
【Fig. 2】
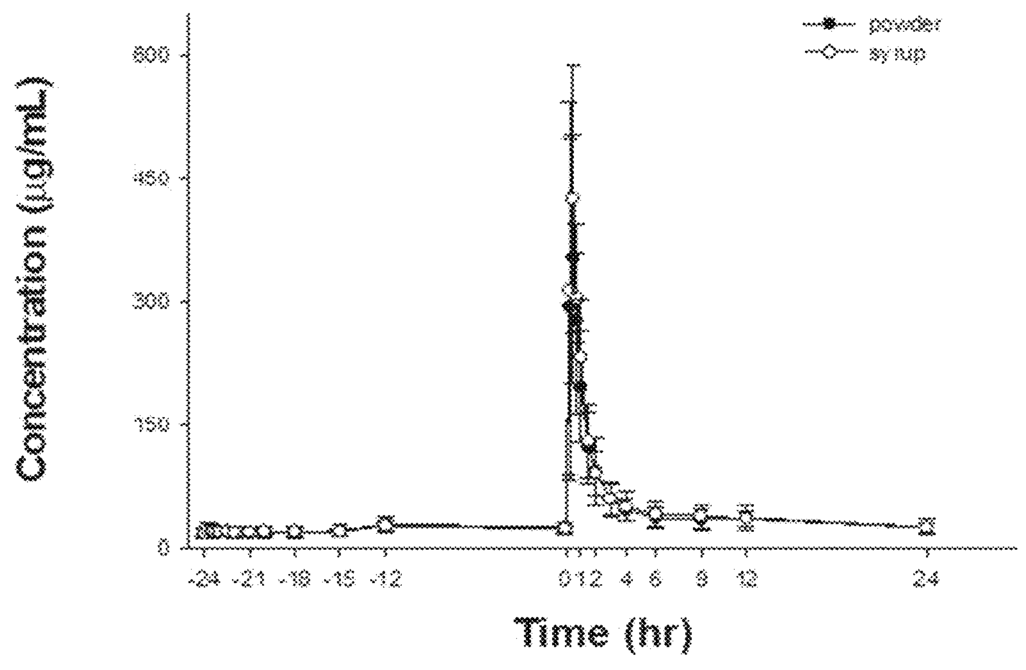

LIQUID PREPARATION OF L-SERINE OR PHARMACEUTICALLY ACCEPTABLE SALT THEREOF AND METHOD FOR PREPARING SAME

CROSS REFERENCE TO RELATED APPLICATIONS

This application is a National Stage of International Application No. PCT/KR2022/003789 filed Mar. 17, 2022, claiming priority based on Korean Patent Application No. 10-2021-0035796 filed Mar. 19, 2021.

TECHNICAL FIELD

The present invention relates to a liquid preparation of L-serine or a pharmaceutically acceptable salt thereof, and a method for preparing the liquid preparation.

BACKGROUND ART

Amino acids are the basic units of proteins constituting living organisms and are likely categorized into 2 types: essential amino acids that are not synthesized by the body and nonessential amino acids that are synthesized by the body.

A total of 20 different amino acids found to date may be broken up into the following two groups on their solubility in water: hydrophilic amino acids such as serine, threonine, tyrosine, and cysteine, and hydrophobic amino acids such as glycine, alanine, valine, leucine, and isoleucine.

In particular, the L form of serine (hereinafter referred to as L-serine) as one of the nonessential amino acids synthesized by the body has a molecular weight of about 105.1 g/mole. L-serine as a hydrophilic amino acid has a solubility limit in water of about 250 mg/ml at 20° C., but a high dose of L-serine in a solution causes discoloration and precipitation over time.

Although L-serine is a nonessential amino acid synthesized by the body, L-serine deficiency may result from multiple causes such as a congenital genetic defect in serine biosynthetic metabolism, hypoxic-ischemic brain injury, and traumatic brain injury. L-serine biosynthesis disorders in the brain may particularly reduce the production of glutathione, which prevents damage caused by reactive oxygen species (ROS), to cause fatal disorders.

Accordingly, it is highly critical for patients having low concentrations of serine in the blood due to decreased or interrupted biosynthesis of L-serine to be directly provided with L-serine instead of other amino acids for treatment.

However, developing a single preparation capable of providing L-serine alone, as well as a preparation containing a high dose or high concentration of L-serine sufficient to bring the L-serine deficiency to a normal level is challenging.

For that reason, a method of administering a large amount of amino acid complex solution containing low concentrations of L-serine to patients who previously had to receive L-serine has been proposed.

In addition, a method of directly taking powder-type or solid-type raw materials has been suggested, but the medication compliance in this case is sharply decreased to reduce therapeutic effects.

Therefore, there remains a need to develop a liquid preparation containing L-serine at a high concentration and available for oral administration.

RELATED ART DOCUMENT

Patent Document 1: Korean Patent No. 10-2091620
Patent Document 2: Korean Patent No. 10-1672347
Non-Patent Document 1: 'Effects of Sample Pretreatment in Amino Acid Analysis', Korean journal of clinical pathology 2001; 21(1): 34-39 (Moon-Hee Kim and Hae-Ran Moon)

DISCLOSURE OF INVENTION

Technical Problem

An object of the present invention is to provide a liquid preparation including L-serine or a pharmaceutically acceptable salt thereof at a high concentration.

The liquid preparation according to the present invention may allow L-serine to be quickly administered and to be taken for a long period of time, and may include L-serine at a high concentration, and accordingly, a total dosage of medicament required for treatment may be reduced to improve medication convenience, oral administration is available as a liquid, and medication compliance of patients is high, resulting in great therapeutic effects.

The liquid preparation according to the present invention may include L-serine or a pharmaceutically acceptable salt thereof at a high concentration with no precipitation or sedimentation of solid materials for a long period of time to have excellent stability in storage stability and long-term storage and may improve the dissolution properties of L-serine to prevent discoloration and recrystallization, resulting in improved safety.

The liquid preparation according to the present invention may keep L-serine or a pharmaceutically acceptable salt thereof in a completely dissolved state for a long period of time, may have a pH that ranges from slightly acidic to neutral with no inclusion of strong acids such as a hydrochloric acid group and a sulfate group, may significantly reduce the total dosage, and may be highly stable and safe to be safely used for a long period of time by patients with diseases including central nervous system diseases, resulting in remarkably high medication convenience and medication compliance.

The liquid preparation according to the present invention has improved bioavailability when administered orally, and is highly stable to have improved ability of maintaining the quality of the preparation during long-term storage and/or use, thereby ensuring excellent therapeutic effects for a long period of time, and provides improved pharmacoeconomics based on physical appearance, improved drug usability, ease of formulation, and a high degree of preparation stabilization.

Another object of the present invention is to provide a method for preparing a liquid preparation including L-serine or a pharmaceutically acceptable salt thereof at a high concentration.

Solution to Problem

1) The present invention relates to a liquid preparation including L-serine or a pharmaceutically acceptable salt thereof as an active component, and a thickener, wherein the preparation has L-serine or a pharmaceutically acceptable salt thereof at a concentration of about 50 mg/mL or greater.

2) In embodiments of 1) according to the present invention, the liquid preparation may have L-serine or a pharmaceutically acceptable salt thereof at a concentration of about 50 mg/mL to about 500 mg/mL.

3) In at least one embodiment of 1) or 2) according to the present invention, the liquid preparation may have L-serine or a pharmaceutically acceptable salt thereof at a concentration of about 70 mg/mL to about 300 mg/mL.

4) In at least one embodiment of 1) to 3) according to the present invention, the thickener included in the liquid preparation may be agar, bentonite, carbomer, sodium carboxymethyl cellulose, carrageenan, microcrystalline sodium carboxymethyl cellulose, guar gum, hydroxyethyl cellulose, hydroxypropyl cellulose, hypromellose, pectin, polyethylene oxide, povidone, corn starch, potato starch, wheat starch, xanthan gum, gelatin, or a mixture thereof.

5) In at least one embodiment of 1) to 4) according to the present invention, the thickener included in the liquid preparation may be sodium carboxymethyl cellulose, povidone, hydroxyethyl cellulose, carbomer, or a mixture thereof.

6) In at least one embodiment of 1) to 5) according to the present invention, the liquid preparation may have the thickener at a concentration of about 0.5 mg/mL to about 100 mg/mL.

7) In at least one embodiment of 1) to 6) according to the present invention, the liquid preparation has a pH of about 4.0 to about 7.0.

8) In at least one embodiment of 1) to 7) according to the present invention, the liquid preparation may further include a buffer.

9) In at least one embodiment of 1) to 8) according to the present invention, the buffer may be borate, acetate, carbonate, citrate, lactate, and hydrate thereof (hydrate of the borate, acetate, carbonate, citrate, or lactate), or a mixture thereof.

10) In at least one embodiment of 1) to 9) according to the present invention, the buffer may be at least one selected from the group consisting of ammonium carbonate, sodium acetate, potassium acetate, calcium carbonate, calcium lactate, potassium citrate, sodium citrate, sodium bicarbonate, sodium lactate, and hydrate thereof.

11) In at least one embodiment of 1) to 10) according to the present invention, the buffer may be a pharmaceutically acceptable salt of citric acid or hydrate thereof.

12) In at least one embodiment of 1) to 11) according to the present invention, the liquid preparation may further include a solvent.

13) In at least one embodiment of 1) to 12) according to the present invention, the liquid preparation may be in the form of a syrup.

14) In at least one embodiment of 1) to 13) according to the present invention, the liquid preparation may further include a sweetener.

15) In at least one embodiment of 1) to 14) according to the present invention, the sweetener may be one selected from the group consisting of acesulfame potassium, aspartame, dextrate, dextrose, fructose, high fructose, galactose, maltose, mannitol, maltitol, xylitol, stevia, steviol glycoside, enzymatically modified stevia, saccharin, saccharin calcium, saccharin sodium, sorbitol, sorbitol solution, sucralose, sucrose, white sugar such as refined white sugar, syrup, simple syrup, honey, and a mixture thereof.

16) In at least one embodiment of 1) to 15) according to the present invention, the liquid preparation may further include a diluent, a solubilizing agent, a flavoring agent, a preservative, a sweetener, an acidifier, a buffer, or a mixture thereof.

17) In at least one embodiment of 1) to 16) according to the present invention, the preservative may be benzoic acid, sodium benzoate, methyl paraoxybenzoate, ethyl paraoxybenzoate, propyl paraoxybenzoate, butyl paraoxybenzoate, sorbic acid, potassium sorbate, sodium sorbate, chlorobutanol, cresol, chlorocresol, or a mixture thereof.

18) The present invention relates to a liquid preparation including L-serine or a pharmaceutically acceptable salt thereof in an amount of about 50 mg/mL to about 500 mg/mL, at least one thickener selected from the group consisting of sodium carboxymethyl cellulose, povidone, hydroxyethyl cellulose, and carbomer, a buffer, and a solvent.

19) In at least one embodiment of 1) to 18) according to the present invention, the liquid preparation may have a pH of about 4.0 to about 7.0.

20) In at least one embodiment of 1) to 19) according to the present invention, the buffer may be borate, acetate, carbonate, citrate, lactate, hydrate of the borate, acetate, carbonate, citrate, or lactate, or a mixture thereof.

21) In at least one embodiment of 1) to 20) according to the present invention, the liquid preparation may further include a diluent, an acidifier, a preservative, a sweetener, or a mixture thereof.

22) The present invention relates to a liquid preparation including L-serine or a pharmaceutically acceptable salt thereof in an amount of about 50 mg/mL to about 500 mg/mL, a thickener selected from sodium carboxymethyl cellulose, povidone, or a mixture thereof, a buffer which is a salt of citric acid, and a solvent which is one selected from the group consisting of water, purified water, water for injection, Ringer's solution, physiological saline, and a mixture thereof.

23) In at least one embodiment of 1) to 22) according to the present invention, the liquid preparation may have a pH of about 4.5 to about 7.0.

24) In at least one embodiment of 1) to 23) according to the present invention, the liquid preparation may be for oral administration, and specifically may be a liquid for internal use.

25) In at least one embodiment of 1) to 24) according to the present invention, the liquid preparation may be a solution.

26) In at least one embodiment of 1) to 25) according to the present invention, the liquid preparation may be for preventing or treating central nervous system diseases.

27) In at least one embodiment of 1) to 26) according to the present invention, the central nervous system diseases may be at least one selected from the group consisting of autism spectrum disorder, Alzheimer's disease, Parkinson's disease, intellectual disability, learning disability, language disorder, attention deficit hyperactivity disorder, emotional disorder, motor disorder, hypoxic-ischemic brain injury, traumatic brain injury, neuroinflammatory disease, cerebrovascular disease, attention disorder, and memory disorder.

28) In at least one embodiment of 1) to 27) according to the present invention, the liquid preparation may be for preventing or treating the autism spectrum disorder.

29) The present invention relates to a method for preparing the liquid preparation including L-serine or a pharmaceutically acceptable salt thereof described above.

30) The present invention relates to a method for preparing the liquid preparation of the present invention described above according to at least one of 1) to 29) above, wherein the method includes:

(1) dissolving a thickener in a solvent to prepare a first solution;

(2) adding a pharmaceutically acceptable first additive to the first solution and heating the mixture to prepare a second solution having a pH of about 4.0 to about 7.0 at about 50° C. or greater; and (3) cooling the second solution, and then dissolving L-serine or a pharmaceutically acceptable salt thereof and a pharmaceutically acceptable second additive in the cooled second solution to prepare a third solution.

31) At least one liquid preparation of 1) to 30) above has L-serine or a pharmaceutically acceptable salt thereof at a concentration of about 50 mg/mL or greater.

32) In at least one embodiment of 1) to 31) according to the present invention, the first additive may include an acidifier, a buffer, a solubilizing agent, a preservative, or a mixture thereof.

33) In at least one embodiment of 1) to 32) according to the present invention, the second additive may include a diluent, a sweetener, a flavoring agent, a coloring agent, or a mixture thereof.

34) The present invention provides a method for treating central nervous system diseases, using the liquid preparation according to 1) to 33) described above, wherein the central nervous system diseases may be at least one selected from the group consisting of autism spectrum disorder, Alzheimer's disease, Parkinson's disease, intellectual disability, learning disability, language disorder, attention deficit hyperactivity disorder, emotional disorder, motor disorder, hypoxic-ischemic brain injury, traumatic brain injury, neuroinflammatory disease, cerebrovascular disease, attention disorder, and memory disorder.

35) The present invention provides a use of the liquid preparation according to 1) to 33) described above for treating central nervous system diseases, wherein the central nervous system diseases may be at least one selected from the group consisting of autism spectrum disorder, Alzheimer's disease, Parkinson's disease, intellectual disability, learning disability, language disorder, attention deficit hyperactivity disorder, emotional disorder, motor disorder, hypoxic-ischemic brain injury, traumatic brain injury, neuroinflammatory disease, cerebrovascular disease, attention disorder, and memory disorder.

36) The present invention provides a use of the liquid preparation according to 1) to 33) described above for preparing a medicament for treating central nervous system diseases, wherein the central nervous system diseases may be at least one selected from the group consisting of autism spectrum disorder, Alzheimer's disease, Parkinson's disease, intellectual disability, learning disability, language disorder, attention deficit hyperactivity disorder, emotional disorder, motor disorder, hypoxic-ischemic brain injury, traumatic brain injury, neuroinflammatory disease, cerebrovascular disease, attention disorder, and memory disorder.

Advantageous Effects of Invention

The liquid preparation according to the present invention may allow L-serine to be quickly administered and to be taken for a long period of time, and may include L-serine at a high concentration, and accordingly, a total dosage of medicament required for treatment may be reduced to improve medication convenience, oral administration is available as a liquid preparation, and medication compliance of patients is high, resulting in great therapeutic effects.

The liquid preparation according to the present invention may include L-serine or a pharmaceutically acceptable salt thereof at a high concentration with no precipitation or sedimentation of solid materials for a long period of time to have excellent stability in storage stability and long-term storage, and may improve the dissolution properties of L-serine to prevent discoloration and recrystallization, resulting in improved safety.

The liquid preparation according to the present invention may keep L-serine or a pharmaceutically acceptable salt thereof in a completely dissolved state for a long period of time, may have a pH that ranges from slightly acidic to neutral with no inclusion of strong acids such as a hydrochloric acid group and a sulfate group, may significantly reduce the total dosage, and may be highly stable and safe to be safely used for a long period of time by patients with diseases including central nervous system diseases, resulting in remarkably high medication convenience and medication compliance.

The liquid preparation according to the present invention has improved bioavailability when administered orally, and is highly stable to have improved ability of maintaining the quality of the preparation during long-term storage and/or use, thereby ensuring excellent therapeutic effects for a long period of time, and provides improved pharmacoeconomics based on physical appearance, improved drug usability, ease of formulation, and a high degree of preparation stabilization.

The liquid preparation according to the present invention may be available for mass production and economically feasible.

BRIEF DESCRIPTION OF DRAWINGS

FIG. 1 is a figure showing the results of an appearance stability test of liquid preparations according to Examples and Comparative Examples of the present invention.

FIG. 2 is a figure showing concentration curves in beagle dog plasma according to the administration of Example preparations of the present invention and control preparations.

BEST MODE FOR CARRYING OUT THE INVENTION

The term "oral preparation" used herein refers to a drug that may be taken, and includes both liquids for oral administration and solids for oral administration.

The term "oral liquids" used herein refers to liquid preparations among preparations for oral administration that may be taken.

The term "oral solids" used herein refers to solid preparations among internal preparations for oral administration that may be taken.

The terms "first", "second", and the like used herein are only used to distinguish between a plurality of components or a plurality of steps, and do not indicate priority.

The present invention relates to a liquid preparation including L-serine or a pharmaceutically acceptable salt thereof as an active component, at a high concentration, and a method for preparing the same.

An embodiment of the present invention relates to a liquid preparation including L-serine or a pharmaceutically acceptable salt thereof.

In embodiments of the present invention, the liquid preparation includes L-serine or a pharmaceutically acceptable salt thereof as an active component, and a thickener.

In embodiments of the present invention, the present invention relates to a liquid preparation including L-serine or a pharmaceutically acceptable salt thereof as an active component, and a thickener, and the liquid preparation may have L-serine or a pharmaceutically acceptable salt thereof at a concentration of about 50 mg/mL or greater.

L-serine or a pharmaceutically acceptable salt thereof is a material having high solubility in water, but a liquid preparation in which L-serine is dissolved at a high concentration of about 50 mg/mL or greater has limitations in pharmaceutical stability, such as discoloration and precipitation caused during storage, and has thus failed to be developed into a liquid preparation including L-serine in an amount of about 50 mg/mL or greater.

The liquid preparation according to the present invention may include L-serine or a pharmaceutically acceptable salt thereof as an active component at a high concentration, and thus is suitable for oral administration and has significantly excellent medication convenience. To be specific, a method of administering a large amount of amino acid complex solution containing low concentrations of L-serine to patients who previously had to receive L-serine has been proposed. However, the amino acid complex solution includes low concentrations of L-serine as well as other types of multiple amino acids. This amino acid complex solution is used as a parenteral nutrition solution serving to supply amino acids for hypoproteinemia, low nutritional status, and before and after surgery, and contains L-serine along with various other amino acids at a low concentration of about 5 mg/mL. When L-serine is administered in a high dose of 10 g or greater through a typical amino acid complex solution, an amount of the solution may be greater 2 L and it takes a long time to administer that amount to a patient. This leads to an increase in treatment costs, and also excessively impedes convenience of drug administration for patients, and causes other amino acids that are not required for the patients to be administered together. In addition, as the solution is administered multiple times over a long period of time, it is not easy to accurately calculate the amount administered to the patients, and oral administration is not applicable, and accordingly, patient medication compliance is significantly low.

The liquid preparation according to the present invention may allow L-serine to be quickly administered and to be taken for a long period of time, and may include L-serine at a high concentration, and accordingly, a total dosage of medicament required for treatment may be reduced to improve medication convenience, oral administration is available as a liquid preparation, resulting in great therapeutic effects with high patient medication compliance.

In addition, the liquid preparation is capable of maintaining the stability as described above for a long period of time while using water as a solvent, and thus is remarkably safe.

The liquid preparation according to the present invention may include L-serine or a pharmaceutically acceptable salt thereof at a high concentration with no precipitation or sedimentation of solid materials for a long period of time to have excellent stability in storage stability and long-term storage, and may improve the dissolution properties of L-serine or a salt thereof to prevent discoloration and recrystallization of L-serine or a salt thereof, resulting in improved safety.

The liquid preparation according to the present invention may keep L-serine or a pharmaceutically acceptable salt thereof in a completely dissolved state for a long period of time, may have a pH that ranges from slightly acidic to neutral with no inclusion of strong acids such as a hydrochloric acid group and a sulfate group, may significantly reduce the total dosage, and may be highly safe to be safely used for a long period of time by patients with diseases including central nervous system diseases.

The liquid preparation according to the present invention has improved bioavailability, and is highly stable and safe to have improved ability of maintaining the quality of the preparation during long-term storage and/or use, thereby ensuring excellent therapeutic effects for a long period of time, maintains a stable liquid state for a long period of time, thereby significantly improving medication compliance, and provides improved pharmacoeconomics based on physical appearance, improved drug usability, ease of formulation, and a high degree of preparation stabilization.

In embodiments of the present invention, L-serine is a compound represented by Formula 1 below, and a source thereof is not particularly limited as long as the compound is usable in liquid preparations.

[Formula 1]

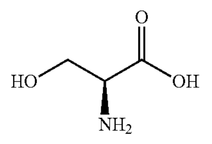

In embodiments of the present invention, the pharmaceutically acceptable salt of L-serine is a salt of L-serine commonly used in the pharmaceutical industry, and is not particularly limited as long as the salt is usable in liquid preparations.

In embodiments of the present invention, the pharmaceutically acceptable salt may be an inorganic salt, an inorganic acid salt, an organic acid salt, sulfonate, and the like of L-serine. These example pharmaceutically acceptable salts may be used alone or two or more of these may be mixed and used. For example, the inorganic salt may be a metal salt including calcium salt, potassium salt, sodium salt, magnesium salt, and the like, the inorganic acid salt may include hydrochloride, nitrate, bromate, iodate, perchlorate, tartrate, sulfate, and the like, the organic acid salt may include acetate, trifluoroacetate, citrate, maleate, succinate, oxalate, benzoate, tartrate, fumarate, manderate, propionate, lactate, glycolate, gluconate, galacturonate, glutamate, glutarate, glucuronate, aspartate, ascorbate, carbonate, vanillate, hydroiodic acid, and the like, and the sulfonate may include methanesulfonate, ethanesulfonate, benzenesulfonate, p-toluenesulfonate, naphthalenesulfonate, and the like.

In an embodiment, the pharmaceutically acceptable salt of L-serine may be a metal salt of L-serine, and may specifically be at least one of calcium salt, potassium salt, sodium salt, or magnesium salt, and the pharmaceutically acceptable salt of L-serine may be magnesium salt.

In embodiments of the present invention, the liquid preparation may include L-serine or a pharmaceutically acceptable salt thereof as an active component at a high concentration, and may specifically include L-serine or a pharmaceutically acceptable salt thereof in an amount of about 50 mg/mL or greater.

In an embodiment, the liquid preparation may include L-serine or a pharmaceutically acceptable salt thereof as an active component at a concentration of about 50 mg/mL to about 500 mg/mL.

In an embodiment, the liquid preparation may include L-serine or a pharmaceutically acceptable salt thereof as an active component at a concentration of about 70 mg/mL to about 300 mg/mL.

In an embodiment, the liquid preparation may include L-serine or a pharmaceutically acceptable salt thereof as an active component at a concentration of about 100 mg/mL to about 200 mg/mL.

For example, the liquid preparation may include L-serine or a pharmaceutically acceptable salt thereof as an active component at a concentration of about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, about 400 mg/mL, about 410 mg/mL, about 420 mg/mL, about 430 mg/mL, about 440 mg/mL, about 450 mg/mL, about 460 mg/mL, about 470 mg/mL, about 480 mg/mL, about 490 mg/mL, about 500 mg/mL and the like.

In embodiments of the present invention, the liquid preparation may include a thickener, which is a pharmaceutically acceptable additive. In this case, the liquid preparation of the present invention may exhibit excellent stability while including L-serine or a pharmaceutically acceptable salt thereof at a high concentration.

In embodiments of the present invention, the thickener is a material that resists liquid-like flow, and may be agar, bentonite, carbomer, sodium carboxymethyl cellulose, carrageenan, microcrystalline sodium carboxymethyl cellulose, guar gum, hydroxyethyl cellulose, hydroxypropyl cellulose, hypromellose, pectin, polyethylene oxide, povidone, corn starch, potato starch, wheat starch, xanthan gum, gelatin, and the like. These example thickeners may be used alone or two or more of these may be mixed and used.

In embodiments of the present invention, the carbomer may be carbomer 971P, carbomer 910, carbomer 934, carbomer 934p, carbomer 940, carbomer 941, carbomer 1342, a carbomer copolymer, a carbomer homopolymer, a carbomer interpolymer, and the like, but is not limited thereto.

For example, the thickener may be sodium carboxymethyl cellulose, povidone, hydroxyethyl cellulose, carbomer, or a mixture thereof.

In embodiments of the present invention, the liquid preparation may have the thickener at a concentration of about 0.5 mg/mL to about 150 mg/mL, specifically about 0.5 mg/mL to about 100 mg/mL, and more specifically about 1 mg/mL to about 100 mg/mL.

In embodiments of the present invention, the liquid preparation may further include a solvent. The solvent is a material that may be dissolved to form a uniformly dispersed mixture (solution) of molecules or ions of an active component L-serine or a pharmaceutically acceptable salt thereof, and is not particularly limited as long as the solvent is usable in liquid preparations.

In embodiments of the present invention, the solvent may be water, purified water, water for injection, Ringer's solution, ethanol, ether, alcohol, white wine, fruit wine, glycerin, peanut oil, physiological saline, and the like, and these example solvents may be used alone or two or more of these may be mixed and used.

In embodiments of the present invention, the solvent may be an aqueous solvent, and for example, the solvent may be water, Ringer's solution, purified water, water for injection, physiological saline, or a mixture thereof.

In embodiments of the present invention, the liquid preparation may have a pH ranging between slightly acidic and neutral, and specifically the liquid preparation may have a pH of about 4.0 to about 7.0. The liquid preparation according to the present invention may remain stable at the above range of pH for a long period of time, may be highly stable, and may provide significantly excellent medication convenience and medication compliance. For example, the liquid preparation of the present invention may have a pH of about 4.5 to about 7.0, may specifically have a pH of about 4.5 to about 6.0, and may more specifically have a pH of about 5.0 to about 6.0, and for example, the liquid preparation may have a pH of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, and the like.

In embodiments of the present invention, the liquid preparation may further include a buffer. In this case, the liquid preparation including L-serine or a pharmaceutically acceptable salt thereof according to the present invention may remain stable for a long period of time while having an appropriate pH for administration, may be highly safe, and may provide significantly excellent dosing convenience and medication compliance.

The buffer is a material added to a solution to prevent a significant change in hydrogen ion index and generally may be a mixture of a weak acid and a salt related thereto or a salt of an acid, and is not particularly limited as long as the material may be usable as a buffer. For example, the buffer may be borate, acetate, carbonate, citrate, lactate, and the like, and may be a hydrate form of each salt described above, or a mixture thereof. In the buffer, one of acetate, carbonate, citrate, lactate, and hydrate thereof may be included, or a mixture of two or more thereof may be included.

For example, the buffer may be ammonium carbonate, sodium acetate, potassium acetate, calcium carbonate, calcium lactate, potassium citrate, sodium citrate, sodium bicarbonate, sodium lactate, and hydrate thereof. These example buffers may be used alone or two or more of these may be mixed and used.

According to embodiments of the present invention, the liquid preparation may not include phosphoric acid or phosphate salts. Phosphoric acid or phosphoric acid salts may cause diarrhea, and accordingly, patients having diseases or reduced stamina, or the weak and the elderly people such as children or seniors may experience side effects such as diarrhea when taking large doses over a long period of time. Therefore, the liquid preparation according to an embodiment of the present invention may not include phosphoric acid or phosphoric acid salts, if necessary.

In embodiments of the present invention, the buffer may be included in an amount having a concentration suitable for maintaining pH, and specifically may be included at a concentration of about 0.5 mg/mL to about 50 mg/mL, but depending on the type of buffer, the concentration may be adjusted appropriately.

In embodiments of the present invention, the liquid preparation may further include a sweetener, and the liquid preparation including L-serine or a pharmaceutically acceptable salt thereof according to the present invention may remain stable in a liquid state for a long period of time while including a sweetener, and thus is highly safe and provides significantly excellent dosing convenience and medication compliance to allow even patients having difficulties taking medications orally, such as children and the elderly, to easily take the medications.

The sweetener is a material for providing a sweet taste, and is not particularly limited as long as the material is usable in liquid preparations. For example, the sweetener may be acesulfame potassium, aspartame, dextrate, dextrose, fructose, high fructose, galactose, maltose, mannitol, maltitol, xylitol, stevia, steviol glycoside, enzymatically modified stevia, saccharin, saccharin calcium, saccharin sodium, sorbitol, sorbitol solution, sucralose, sucrose, white sugar such as refined white sugar, syrup, simple syrup, honey, and the like. These example sweeteners may be used alone or two or more of these may be mixed and used.

The taste of the liquid preparation according to an embodiment of the present invention may be improved by adding a sweetener, thereby significantly increasing medication convenience for children. In addition, the addition of such sweeteners may provide excellent stability, safety, and therapeutic effects.

In embodiments of the present invention, the liquid preparation may further include additional additives in addition to thickeners, buffers, and/or sweeteners, and the additional additives may be a diluent, an acidifier, a preservative, or a mixture thereof.

In embodiments of the present invention, the liquid preparation may further include additional additives in addition to thickeners, buffers, and/or sweeteners, and the additional additives may be a diluent, a solubilizing agent, a stabilizer, a flavoring agent, a coloring agent, a preservative, a foaming agent, a freshening agent, an antiseptic, a flavor enhancer, or a mixture thereof.

The diluent is a material other than a solvent to increase the capacity of the liquid preparation, and is not particularly limited as long as the material is usable in the liquid preparation. For example, the diluent may be sugar, sugar alcohol, glycol, or a mixture thereof, and specifically may be hexylene glycol, propylene glycol, sorbitol, sorbitan, sorbitol solution, mannitol, lactose, and the like. These example diluents may be used alone or two or more of these may be mixed and used.

The solubilizing agent is a liquid material for increasing the solubility of all components, and is not particularly limited as long as the material is usable in liquid preparations. For example, the solubilizing agent may be monostearate sucrose, polyoxyethylene sorbitol fatty acid ester (twin ester), polyoxyethylene monoalkyl ether, lanolin ether, lanolin ester, and the like, and for example, may be polysorbate. These example solubilizing agents may be used alone or two or more of these may be mixed and used.

The stabilizer is a material added to prevent deterioration of flavor and delay oxidation, or a material for preventing evaporation and deterioration of volatile flavor, and is not particularly limited as long as the material is usable in liquid preparations. The liquid preparation of the present invention may exhibit sufficient stability for a long period of time without the addition of a stabilizer, but may be optionally added to maintain flavor or taste.

The stabilizer may be an alkalizing agent including ammonia water, potassium hydroxide, sodium hydroxide, prolamine, and the like. These example stabilizers may be used alone or two or more of these may be mixed and used.

The flavoring agent is a material for adding a specific flavor, and is not particularly limited as long as the material is usable in liquid preparations. For example, the flavoring agent may be almond oil, anethole, benzaldehyde, ethyl acetate, ethyl vanillin, lactitol, maltol, menthol, methyl salicylate, monosodium glutamate, peppermint, peppermint oil, peppermint alcohol, rose oil, and strong rose water, thymol, vanillin, and the like. These example flavoring agents may be used alone or two or more of these may be mixed and used.

The coloring agent is a material for imparting color, and is not particularly limited as long as the material is usable in liquid preparations. For example, the coloring agent may be caramel, iron oxide (red, yellow, mixed), and the like. In addition, for example, tar colors for drugs, quasi-drugs, and cosmetics according to Food and Drug Administration Notice No. 2000-66 may be used. These example coloring agents may be used alone or two or more of these may be mixed and used.

The preservative is a material used to protect all components from spoilage, discoloration, corrosion, and the like, or to delay or prevent microbial or chemical spoilage, and is not particularly limited as long as the material is usable in liquid preparations. For example, the preservative may be benzoic acid, sodium benzoate, methyl paraoxybenzoate, ethyl paraoxybenzoate, propyl paraoxybenzoate, butyl paraoxybenzoate, sorbic acid, potassium sorbate, sodium sorbate, chlorobutanol, cresol, chlorocresol, and the like. These example preservatives may be used alone or two or more of these may be mixed and used.

The foaming agent is a material for increasing the amount of air in a preparation, and is not particularly limited as long as the material is usable in liquid preparations. For example, the foaming agent may be sodium bicarbonate, sodium carbonate, magnesium carbonate, ammonium bicarbonate, ammonium carbonate, potassium carbonate, calcium carbonate, and the like. These example foaming agents may be used alone or two or more of these may be mixed and used.

The refreshing agent is a material for providing a refreshing feeling, and is not particularly limited as long as the material is usable in liquid preparations. For example, the refreshing agent may be d-camphor, dl-camphor, l-menthol, dl-menthol, peppermint oil, eucalyptus oil, and the like. These example refreshing agents may be used alone or two or more of these may be mixed and used.

The flavor enhancer is a material for maximizing or adjusting the original taste and flavor without changing the original flavor, and is not particularly limited as long as the material is usable in liquid preparations. For example, the flavor enhancer may be white sugar, citric acid, monosodium glutamate, peppermint oil, and the like. These example flavor enhancers may be used alone or two or more of these may be mixed and used.

In embodiments of the present invention, the liquid preparation may include L-serine or a pharmaceutically acceptable salt thereof as an active component in an amount of about 50 mg/mL or greater, a thickener, a buffer, and a solvent.

In embodiments of the present invention, the liquid preparation may include L-serine or a pharmaceutically acceptable salt thereof as an active component in an amount of about 50 mg/mL or greater, a thickener, a buffer, and a sweetener.

In embodiments of the present invention, the liquid preparation may include L-serine or a pharmaceutically acceptable salt thereof as an active component in an amount of about 50 mg/mL or greater, a thickener, a buffer, a sweetener, and a solvent. In embodiments of the present invention, the liquid preparation may further include at least one of a diluent, a flavoring agent, a preservative, a sweetener, and an acidifier, in addition to L-serine or a pharmaceutically acceptable salt thereof as an active component in an amount of about 50 mg/mL or greater, a thickener, a buffer, a sweetener, and a solvent.

In embodiments of the present invention, the liquid preparation may further include at least one selected from the group consisting of a diluent, a flavoring agent, a preservative, a sweetener, an acidifier, and a solubilizing agent, in addition to L-serine or a pharmaceutically acceptable salt thereof as an active component in an amount of about 50 mg/mL or greater, a thickener, a buffer, a sweetener, and a solvent.

In embodiments of the present invention, the liquid preparation may further include at least one selected from the group consisting of a diluent, a flavoring agent, a preservative, a sweetener, an acidifier, and a solubilizing agent, a solubilizer, and a stabilizer, in addition to L-serine or a pharmaceutically acceptable salt thereof as an active component in an amount of about 50 mg/mL to about 500 mg/mL, a thickener, a buffer, a sweetener, and a solvent.

In embodiments of the present invention, the liquid preparation may include L-serine or a pharmaceutically acceptable salt thereof in an amount of about 50 mg/mL to about 500 mg/mL, at least one thickener selected from the group consisting of sodium carboxymethyl cellulose, povidone, hydroxyethyl cellulose, and carbomer, a buffer, and a solvent. The liquid preparation may have a pH of about 4.0 to about 7.0. In this case, the types of buffer and solvent are the same as previously described. In addition, the liquid preparation may further include at least one of a diluent, an acidifier, a preservative, a sweetener, and a mixture thereof, if necessary.

In embodiments of the present invention, the liquid preparation may include L-serine or a pharmaceutically acceptable salt thereof in an amount of about 50 mg/mL to about 500 mg/mL, a thickener selected from sodium carboxymethyl cellulose, povidone, or a mixture thereof, a buffer which is a salt of citric acid, and a solvent which is one selected from the group consisting of water, purified water, water for injection, Ringer's solution, physiological saline, and a mixture thereof. The liquid preparation may have a pH of about 4.0 to about 7.0.

In embodiments of the present invention, the liquid preparation may include L-serine or a pharmaceutically acceptable salt thereof in an amount of about 50 mg/mL to about 300 mg/mL, a thickener which is sodium carboxymethyl cellulose, a buffer which is a salt of citric acid, and a solvent which is one selected from the group consisting of water, purified water, water for injection, Ringer's solution, physiological saline, and a mixture thereof, and the liquid preparation may have a pH of about 4.0 to about 7.0.

In an embodiment, the liquid preparation may include additives such as a thickener, a buffer, a sweetener, a diluent, a flavoring agent, a preservative, a sweetener, an acidifier, and a solubilizing agent, each independently at a concentration of about 0.001 mg/mL or greater or about 0.01 mg/mL to about 150 mg/mL. For example, the liquid preparation may include the additives each independently at a concentration of about 0.001 mg/mL, about 0.01 mg/mL, about 0.1 mg/mL, about 0.5 mg/mL, about 1 mg/mL, about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, and the like.

In embodiments of the present invention, the liquid preparation may be for oral use or parenteral use. The liquid preparation may be specifically for oral use or oral administration, and more specifically may be an oral solution, for example, an oral liquid.

In embodiments of the present invention, the liquid preparation may be syrup, elixir, spirit, medicated water, or lemonade, and may specifically be syrup or lemonade, and may more specifically be syrup.

In embodiments of the present invention, the liquid preparation may be in a solution state, and specifically may be a transparent solution.

The liquid preparation according to the present invention is highly stable, and a stability test for 3 months in accelerated test conditions (temperature: 40±2° C., relative humidity: 75±5%) showed significantly excellent appearance stability and content stability (Experimental Example 1 and FIG. 1; and Experimental Example 2).

The liquid preparation according to the present invention showed high blood concentration when administered orally, providing excellent therapeutic effects, and when administered to beagle dogs, the liquid preparation showed an excellent PK profile compared to a control preparation in which powder-type L-serine at the same concentration was added to water (Experimental Example 3 and FIG. 2).

The liquid preparation including L-serine or a pharmaceutically acceptable salt thereof of the present invention described above may be used for preventing or treating central nervous system diseases.

In embodiments of the present invention, the central nervous system diseases may be at least one selected from the group consisting of autism spectrum disorder, Alzheimer's disease, Parkinson's disease, intellectual disability, learning disability, language disorder, attention deficit hyperactivity disorder, emotional disorder, motor disorder, hypoxic-ischemic brain injury, traumatic brain injury, neuroinflammatory disease, cerebrovascular disease, attention disorder, and memory disorder, specifically may be autism spectrum disorder, Alzheimer's, and/or Parkinson's disease, and more specifically may be autism spectrum disorder.

In embodiments of the present invention, the liquid preparation may be used for preventing or treating autism spectrum disorder.

Another embodiment of the present invention relates to a method for preparing the liquid preparation described above.

The present invention relates to a method for preparing a liquid preparation including L-serine or a pharmaceutically acceptable salt thereof at a high concentration, and the liquid preparation has L-serine or a pharmaceutically acceptable salt thereof at a concentration of about 50 mg/mL or greater.

In embodiments of the present invention, the method for preparing a liquid preparation of L-serine or a pharmaceutically acceptable salt thereof may include dissolving an active component, an additive, or a combination thereof in a solvent.

The method for preparing the liquid preparation according to the present invention may include:

(1) dissolving a thickener in a solvent to prepare a first solution;

(2) adding a pharmaceutically acceptable first additive to the first solution and heating the mixture to prepare a second solution having a pH of about 4.0 to about 7.0 at a temperature of 50° C. or greater; and (3) cooling the second solution, and then dissolving L-serine or a pharmaceutically acceptable salt thereof and a pharmaceutically acceptable second additive in the cooled second solution to prepare a third solution.

The liquid preparation has L-serine or a pharmaceutically acceptable salt thereof at a concentration of about 50 mg/mL or greater.

The preparation method of the present invention may mass-produce highly stable liquid preparations including L-serine or a pharmaceutically acceptable salt thereof at a high concentration through a simple method, and thus, it is economical and commercially excellent.

In the preparation method above, when the active components, the additives, and the like are each more than one type as needed, the order of addition may be adjusted according to the characteristics of the components included in the liquid preparation.

In embodiments of the present invention, a pharmaceutically acceptable first additive may be one or a mixture of two or more selected from the group consisting of an acidifier, a buffer, a preservative, and a solubilizing agent.

In embodiments of the present invention, a pharmaceutically acceptable second additive may be a diluent, a sweetener, a flavoring agent, a coloring agent, or a mixture thereof.

In embodiments of the present invention, in the preparation method, an additional pharmaceutically acceptable third additive may be further added in addition to the first and second additives, when needed. Specifically, the method for preparing the liquid preparation may further include adding the pharmaceutically acceptable third additive to the third solution.

In embodiments of the present invention, the pharmaceutically acceptable third additive may be the same as or different from the first additive and/or the second additive, and specifically, the third additive may be different from the first additive and/or the second additive. For example, the third additive may be a thickener, a buffer, a sweetener, a diluent, an acidifier, a preservative, a solubilizing agent, a stabilizer, a flavoring agent, a coloring agent, a foaming agent, a freshening agent, an antiseptic, a flavor enhancer, or a mixture thereof.

In embodiments of the present invention, the heating temperature in step (1) may be about 50° C. to about 80° C.

In embodiments of the present invention, the cooling temperature in step (2) may be less than about 50° C. or about 4° C. to about 50° C.

In the preparation method, the temperature at which active components, additives, and the like are dissolved in a solvent may be adjusted according to the characteristics of each component.

In the preparation method according to the present invention, various physical properties including active components in a liquid preparation and concentrations thereof, types of additives and concentrations thereof, and pH of the liquid preparation may be substantially the same as those described in the liquid formulation according to the present invention as long as the physical properties do not contradict each other.

As for the description of the liquid preparation and the method for preparing the liquid preparation described herein, the description shown in any one may be equally applied to the other as long as the descriptions do not contradict each other.

MODE FOR THE INVENTION

Hereinafter, the present invention is explained in detail by Examples. The following Examples are intended to further illustrate the present invention without limiting its scope.

EXAMPLE

Hereinafter, preferred examples according to the present invention are provided to aid in understanding of the present invention. However, the following Examples are provided only to make the present invention easier to understand, and the content of the present invention is not limited by Examples.

As for components used in Examples, products such as L-serine (Tianjin Tianyao, China), D-sorbitol solution (PAIK KWANG INDUSTRIAL CO., LTD, Korea), Carbomer 971P (Lubrizol, USA), hydroxyethyl cellulose (Ashland, USA), povidone K-30 (BASF, Germany), sodium carboxymethyl cellulose (Patel chem, India), Tween 20 (SAMCHUN PURE CHEMICAL, Korea), apple mint flavored SJ-G (22005221) (SAMJUNG FLAVOR, Korea), methyl paraoxybenzoate (SAN Fu chemical, Taiwan), propyl paraoxybenzoate (SAN Fu chemical, Taiwan), refined white sugar (Nexpharm Korea, Korea), citric acid hydrate (SAMCHUN PURE CHEMICAL, Korea), potassium citrate hydrate (SAMCHUN PURE CHEMICAL, Korea), sodium citrate hydrate (SAMCHUN PURE CHEMICAL, Korea), sucralose (WHAWON PHARM, Korea), aspartame (DAESHIN PHARM, Korea), enzymatically modified stevia (Wako pure chemical, Japan), and acesulfame potassium (WHAWON PHARM, Korea) were purchased and used.

Example 1: Preparation of Liquid Preparation 1 (Examples 1-1 to 1-6)

A liquid preparation containing L-serine at a concentration of 100 mg/mL was prepared according to the components and content listed in Table 1 below. The content listed in Table 1 indicates an amount (mg) contained per 1 mL of liquid.

First, a thickener was swollen in purified water and then dissolved. A preservative, an acidifier, a buffer, and a solubilizing agent were completely dissolved at a heating temperature of 50° C. or greater to set the pH to 4.0 to 7.0. Thereafter, the solution was cooled to less than 50° C., and then L-serine, a diluent, a sweetener, and the like were added and dissolved. All were dissolved, and then a coloring agent or a flavoring agent were added, and the volume was adjusted with purified water to prepare a syrup for oral administration containing L-serine.

TABLE 1

| Content (amount in 1 mL (mg)) | | Example | Example | Example | Example | Example | Example |
|---|---|---|---|---|---|---|---|
| Function | Component | 1-1 | 1-2 | 1-3 | 1-4 | 1-5 | 1-6 |
| Active component | L-serine | 100.0 | 100.0 | 100.0 | 100.0 | 100.0 | 100.0 |
| Diluent | D-sorbitol solution | 30.0 | 30.0 | 30.0 | 30.0 | 30.0 | 30.0 |
| Thickener | Carbomer 971P | 4.0 | — | — | — | — | — |
| | Hydroxyethyl cellulose (250HHX) | — | 2.0 | — | — | — | — |
| | Povidone K-30 | — | — | 10.0 | 10.0 | — | — |
| | Sodium carboxymethyl cellulose | — | — | — | 2.0 | 2.0 | 2.0 |
| Solubilizing agent | Polyoxyethylene sorbitol fatty acid ester (Tween 20) | — | — | — | — | 1.0 | — |
| Flavoring agent | Apple mint flavored SJ-G (22005221) | 2.0 | 2.0 | 2.0 | 2.0 | 2.0 | 2.0 |
| Preservative | Methyl paraoxybenzoate | 0.05 | 0.05 | 0.05 | 0.05 | 0.05 | 0.05 |
| | Propyl paraoxybenzoic acid | 0.05 | 0.05 | 0.05 | 0.05 | 0.05 | 0.05 |
| Sweetener | Refined white sugar | 80.0 | 80.0 | 80.0 | 80.0 | 80.0 | 80.0 |
| Acidifier | Citric acid hydrate | 0.3 | 0.3 | 0.3 | 0.3 | 0.3 | 0.3 |
| Buffer | Potassium citrate hydrate | 1.5 | — | — | 1.5 | 1.5 | 1.5 |
| | Sodium citrate hydrate | — | 1.5 | 1.5 | — | — | — |
| Solvent | Purified water | q.s | q.s | q.s | q.s | q.s | q.s |
| | Final pH | 5.4 | 5.5 | 5.6 | 5.6 | 5.4 | 5.6 |

Example 2: Preparation of Liquid Preparation 2 (Examples 2-1 to 2-6)

Liquid preparations containing L-serine (Examples 2-1 to 2-6) at different concentrations were prepared in substantially the same manner as the preparation method described in Example 1 according to the components and content listed in Table 2 below.

The content listed in Table 2 indicates an amount (mg) contained per 1 mL of liquid preparation.

TABLE 2

| Content (amount in 1 mL (mg)) | | Example | Example | Example | Example | Example | Example |
|---|---|---|---|---|---|---|---|
| Function | Component | 2-1 | 2-2 | 2-3 | 2-4 | 2-5 | 2-6 |
| Active component | L-serine | 50.0 | 75.0 | 150.0 | 200.0 | 250.0 | 300.0 |
| Diluent | D-sorbitol solution | 30.0 | 30.0 | 30.0 | 30.0 | 30.0 | 30.0 |
| Thickener | Sodium carboxymethyl cellulose | 2.0 | 2.0 | 2.0 | 2.0 | 2.0 | 2.0 |
| Flavoring agent | Apple mint flavored SJ-G (22005221) | 2.0 | 2.0 | 2.0 | 2.0 | 2.0 | 2.0 |
| Preservative | Methyl paraoxybenzoate | 0.05 | 0.05 | 0.05 | 0.05 | 0.05 | 0.05 |
| | Propyl paraoxybenzoic acid | 0.05 | 0.05 | 0.05 | 0.05 | 0.05 | 0.05 |
| Sweetener | Refined white sugar | 80.0 | 80.0 | 80.0 | 80.0 | 80.0 | 80.0 |
| Acidifier | Citric acid hydrate | 0.3 | 0.3 | 0.3 | 0.3 | 0.3 | 0.3 |
| Buffer | Potassium citrate hydrate | 1.5 | 1.5 | 1.5 | 1.5 | 1.5 | 1.5 |
| Solvent | Purified water | q.s | q.s | q.s | q.s | q.s | q.s |
| | Final pH | 5.2 | 5.3 | 5.7 | 5.8 | 5.8 | 5.9 |

Example 3: Preparation of Liquid Preparation 3 (Examples 3-1 to 3-6)

According to the components and content listed in Table 3 below, liquid preparations containing L-serine at a concentration of 100 mg/mL (Examples 3-1 to 3-6) were prepared in substantially the same manner as the preparation method described in Example 1. The content listed in Table 3 indicates an amount (mg) contained per 1 mL of liquid preparation.

TABLE 3

| Content (amount in 1 mL (mg)) | | Example | Example | Example | Example | Example | Example |
|---|---|---|---|---|---|---|---|
| Function | Component | 3-1 | 3-2 | 3-3 | 3-4 | 3-5 | 3-6 |
| Active component | L-serine | 100.0 | 100.0 | 100.0 | 100.0 | 100.0 | 100.0 |
| Diluent | D-sorbitol solution | 30.0 | 30.0 | 30.0 | 30.0 | 30.0 | 30.0 |

TABLE 3-continued

| Content (amount in 1 mL (mg)) | | Example | Example | Example | Example | Example | Example |
|---|---|---|---|---|---|---|---|
| Function | Component | 3-1 | 3-2 | 3-3 | 3-4 | 3-5 | 3-6 |
| Thickener | Sodium carboxymethyl cellulose | 0.5 | 5.0 | — | — | 2.0 | 2.0 |
| | Povidone K-30 | — | — | 50.0 | 100.0 | — | — |
| Flavoring agent | Apple mint flavored SJ-G (22005221) | 2.0 | 2.0 | 2.0 | 2.0 | 2.0 | 2.0 |
| Preservative | Methyl paraoxybenzoate | 0.05 | 0.05 | 0.05 | 0.05 | 0.05 | 0.05 |
| | Propyl paraoxybenzoic acid | 0.05 | 0.05 | 0.05 | 0.05 | 0.05 | 0.05 |
| Sweetener | Refined white sugar | 80.0 | 80.0 | 80.0 | 80.0 | 80.0 | 80.0 |
| Acidifier | Citric acid hydrate | 0.3 | 0.3 | 0.3 | 0.3 | 0.3 | 0.3 |
| Buffer | Potassium citrate hydrate | 1.5 | 1.5 | 1.5 | 1.5 | 0.5 | 10.0 |
| Solvent | Purified water | q.s | q.s | q.s | q.s | q.s | q.s |
| | Final pH | 5.4 | 5.5 | 5.4 | 5.6 | 5.7 | 5.1 |

Example 4: Preparation of Liquid Preparation 4 (Examples 4-1 to 4-6)

According to the components and content listed in Table 4 below, liquid preparations containing L-serine (Examples 4-1 to 4-6) were prepared in substantially the same manner as the method described in Example 1. The content listed in Table 4 indicates an amount (mg) contained per 1 mL of liquid preparation.

TABLE 4

| Content (amount in 1 mL (mg)) | | Example | Example | Example | Example | Example | Example |
|---|---|---|---|---|---|---|---|
| Function | Component | 4-1 | 4-2 | 4-3 | 4-4 | 4-5 | 4-6 |
| Active component | L-serine | 100.0 | 100.0 | 100.0 | 200 | 200 | 200 |
| Diluent | D-sorbitol solution | 1.0 | 1.0 | 1.0 | 1.0 | 1.0 | 1.0 |
| Thickener | Sodium carboxymethyl cellulose | 2.0 | 2.0 | 2.0 | 2.0 | 2.0 | 2.0 |
| Flavoring agent | Apple mint flavored SJ-G (22005221) | 2.0 | 2.0 | 2.0 | 2.0 | 2.0 | 2.0 |
| Preservative | Methyl paraoxybenzoate | 0.05 | 0.05 | 0.05 | 0.05 | 0.05 | 0.05 |
| | Propyl paraoxybenzoic acid | 0.05 | 0.05 | 0.05 | 0.05 | 0.05 | 0.05 |
| Sweetener | Refined white sugar | 0.8 | 0.8 | 0.8 | 0.8 | 0.8 | 0.8 |
| | Sucralose | 0.5 | — | 0.2 | 0.2 | 0.2 | 0.2 |
| | Aspartame | 0.2 | 0.2 | — | — | 0.2 | 0.2 |
| | Enzymatically modified stevia | — | 0.5 | 0.5 | 0.5 | 0.5 | 0.5 |
| | Acesulfame potassium | — | — | — | 0.2 | — | 0.2 |
| Acidifier | Citric acid hydrate | 0.3 | 0.3 | 0.3 | 0.3 | 0.3 | 0.3 |
| Buffer | Potassium citrate hydrate | 1.5 | 1.5 | 1.5 | 1.5 | 0.5 | 1.5 |
| Solvent | Purified water | q.s | q.s | q.s | q.s | q.s | q.s |
| | Final pH | 5.4 | 5.5 | 5.5 | 5.5 | 5.6 | 5.5 |

Comparative Examples 1 to 3

Liquid preparations containing L-serine (Comparative Examples 1 to 3) were prepared in substantially the same manner as the method described in Example 1 according to the components and content listed in Table 5 below. The content listed in Table 5 indicates an amount (mg) contained per 1 mL of liquid preparation.

TABLE 5

| | | Content (amount in 1 mL (mg)) | | |
|---|---|---|---|---|
| Function | Component | Comparative Example 1 | Comparative Example 2 | Comparative Example 3 |
| Active component | L-serine | 100.0 | 100.0 | 100.0 |
| Diluent | D-sorbitol solution | — | 30.0 | 30.0 |
| Thickener | Sodium carboxymethyl cellulose | — | — | 2.0 |
| Flavoring agent | Apple mint flavored SJ-G (22005221) | — | 2.0 | 2.0 |
| Preservative | Methyl paraoxybenzoate | — | 0.05 | 0.05 |
| | Propyl paraoxybenzoic acid | — | 0.05 | 0.05 |
| Sweetener | Refined white sugar | — | 80.0 | 80.0 |
| Acidifier | Citric acid hydrate | — | 0.3 | — |
| | Phosphoric acid | — | — | 10.0 |

TABLE 5-continued

| Function | Component | Content (amount in 1 mL (mg)) Comparative Example 1 | Comparative Example 2 | Comparative Example 3 |
|---|---|---|---|---|
| Buffer | Potassium citrate hydrate | — | 1.5 | 1.5 |
| Solvent | Purified water | q.s | q.s | q.s |
| | Final pH | 5.8 | 5.5 | 2.2 |

Experimental Example 1: Appearance Stability Test

The liquid preparations prepared through Examples and Comparative Examples were tested for stability for 3 months in accelerated test conditions (temperature: 40±2° C., relative humidity: 75±5%).

The stability test results for Example 1 described above are shown in Table 6 below.

In addition, the stability test results for Examples 1-6, 2-1, 2-6, and 3-4 according to the present invention and Comparative Examples 1 to 3 are shown in Table 7 and FIG. 1 below.

TABLE 6

| Item | Standard | Example 1-1 | Example 1-2 | Example 1-3 | Example 1-4 |
|---|---|---|---|---|---|
| Appearance | Colorless and transparent solution | Pass | Pass | Pass | Pass |
| Precipitation | No precipitation | N | N | N | N |

TABLE 7

| Item | Standard | Example 1-6 | Example 2-1 | Example 2-6 | Example 3-4 | Comparative Example 1 | Comparative Example 2 | Comparative Example 3 |
|---|---|---|---|---|---|---|---|---|
| Formulation | Colorless and transparent solution | Pass | Pass | Pass | Pass | Fail | Fail (yellow) | Fail (brown) |
| Precipitation | No precipitation | N | N | N | N | Y | Y | Y |

As seen in Table 6, Table 7, and FIG. 1, the liquid preparations prepared according to Examples of the present invention remained in a transparent state, indicating that appearances were all found to be stable in the accelerated test conditions.

On the other hand, it was found that as for the preparation of Comparative Example 1 in which only the main ingredient was dissolved, precipitation in the form of solid particles was shown; the preparation of Comparative Example 2, having no thickener, was discolored into yellow, and precipitation in the form of solid particles was shown; and the preparation of Comparative Example 3, having a pH of 2.2, was discolored into brown and dark brown and precipitation in the form of solid particles was shown, resulting in poor stability.

Experimental Example 2: Content Stability Test

The preparations prepared through Examples and Comparative Examples were stored for 3 months in the long-term storage test conditions (temperature: 25±2° C., relative humidity: 60±5%), and then evaluated for the content (%) using the following analysis method, and the results are shown in Table 8.

[L-Serine Content Test Method]

In the liquid preparations prepared in Examples and Comparative Examples, the equivalent amount of 100 mg of L-serine was placed into a 100 mL-volume flask, and purified water was added to make 100 mL for using the mixture as a sample solution.

Separately, 100 mg of L-serine standard (Sigma, USA) was placed into a 100 mL-volume flask, and then purified water was added to make 100 mL for using the mixture as a standard solution. The amount of L-serine was calculated by testing 10 uL of the standard solution and the sample solution according to a liquid chromatography method in the following conditions.

<HPLC Operating Conditions>

Column: SIELC Primesep 100 (4.6×150 mm, 5 um)

Detector: Ultraviolet aabsorptiometry (reference wavelength: 200 nm)

Flow rate. 1.0 mL/min

Column temperature: Constant temperature of around 30° C.

Mobile phase: Adding phosphoric acid to 1 L of purified water and adjusting pH to 2.2.

Holding time: 60 minutes

TABLE 8

| Test preparation | Standard | Content test result (%) 0 months | After 3 months | Change(%) |
|---|---|---|---|---|
| Example 1-6 | 90.0~130.0% | 107.2 | 106.5 | −0.7 |
| Example 2-1 | | 104.2 | 103.9 | −0.3 |
| Example 2-6 | | 103.6 | 103.1 | −0.5 |

TABLE 8-continued

| Test preparation | Standard | Content test result (%) 0 months | After 3 months | Change(%) |
|---|---|---|---|---|
| Example 3-4 | | 105.3 | 104.3 | −1.0 |
| Comparative Example 1 | | 103.2 | 42.5 | −60.7 |
| Comparative Example 2 | | 106.5 | 84.6 | −21.9 |
| Comparative Example 3 | | 104.5 | 23.1 | −81.4 |

As shown in Table 8, the liquid preparations of Examples (Examples 1-6, 2-1, 2-6, and 3-4) containing L-serine in an amount of 50 mg/mL to 300 mg/mL remained in the standard content range even after 3 months, showing excellent content stability.

On the other hand, the liquid preparations according to Comparative Examples 1, 2, and 3 showed a significant decrease (below the standard) in content after 3 months, resulting in poor appearance and content stabilities. In particular, it was found that Comparative Example 1 containing only an active component and no additives, and Comparative Example 3 having a strongly acidic pH showed a very severe decrease in content.

Experimental Example 3: Animal PK Test

The liquid preparation (syrup) prepared in Examples 1-6 and a control preparation prepared by dissolving L-serine powder in purified water immediately before administration were prepared. In this case, the concentration of L-serine in the control preparation was the same as that in the liquid preparation of Examples 1-6.

The liquid preparation of Examples 1-6 (administered to the experimental group) and the control preparation (administered to the control group) were each administered orally to a total of 12 beagle dogs in the form of cross-administration in 2 groups (6 dogs in each group) in 2 stages, and then Kyungpook National University College of Pharmacy measured the blood L-serine concentration profile and evaluated pharmacokinetics.

As L-serine is an endogenous drug present in the body, blood was collected for a certain period of time before administration and blood was collected after administration. A beagle dog weighing about 10 kg was stopped eating a certain period of time before administration, and blood was collected at 0, 0.25, 0.5, 0.75, 1.0, 1.5, 2, 3, 4, 6, 9, 12, and 24 hours, and then each experimental agent was administered orally at a dose of 40 mL/4 g/head, and then blood was collected at the same time point.

The PK test results for the beagle dog were shown in Table 9 and FIG. 2 below.

The analysis of L-serine in samples was conducted using LC-MS/MS after pretreating plasma samples through a protein precipitation method by partially changing the analysis method reported in 'Effects of Sample Pretreatment in Amino Acid Analysis', Korean journal of clinical pathology 2001; 21(1): 34-39 (Moon-Hee Kim and Hae-Ran Moon).

TABLE 9

| PK item | Example 1~6 (syrup) | Control preparation (Powder) |
|---|---|---|
| $AUC_{last}$ (h*ug/mL) | 1245.1 ± 311.0(CV: 25.0%) | 1183.4 ± 348.1 (CV: 29.4%) |
| $C_{max}$ (ug/mL) | 479.9 ± 157.3(CV: 32.8%) | 417.4 ± 152.1 (CV: 36.4%) |
| $T_{max}$ (hr) | 0.50 (0.25~0.75) | 0.38 (0.25~1.00) |
| $T_{1/2}$ (hr) | 18.4 ± 11.0 | 14.7 ± 5.8 |

As seen in Table 9 and FIG. 2, Examples 1-6 according to the present invention showed higher blood concentration ($C_{max}$) and area under the blood concentration curve (AUC) than the control preparation administered by dissolving L-serine powder immediately before administration, indicating that Examples 1-6 had a relatively high bioavailability. Examples 1-6 was shown to have a smaller CV (coefficient of variation), which represents the deviation according to oral administration, than the control preparation, confirming that the test preparation would show a certain effect by reducing the deviation between individuals.

The invention claimed is:

1. A liquid preparation comprising:

L-serine or a pharmaceutically acceptable salt thereof as an active component;

a thickener; and a buffer, wherein the liquid preparation comprises the L-serine or a pharmaceutically acceptable salt thereof at a concentration of about 50 mg/mL or greater, wherein the thickener is one selected from the group consisting of agar, bentonite, carbomer, sodium carboxymethyl cellulose, carrageenan, microcrystalline sodium carboxymethyl cellulose, guar gum, hydroxyethyl cellulose, hydroxypropyl cellulose, hypromellose, pectin, polyethylene oxide, povidone, corn starch, potato starch, wheat starch, xanthan gum, gelatin, and a mixture thereof, wherein the liquid preparation has a pH of 4.0 to 7.0, and wherein the liquid preparation is an oral preparation.

2. The liquid preparation of claim 1, wherein the L-serine or a pharmaceutically acceptable salt thereof is present at a concentration of about 50 mg/mL to about 500 mg/mL.

3. The liquid preparation of claim 1, wherein the L-serine or a pharmaceutically acceptable salt thereof is present at a concentration of about 70 mg/mL to about 300 mg/mL.

4. The liquid preparation of claim 1, wherein the thickener is one selected from the group consisting of sodium carboxymethyl cellulose, povidone, hydroxyethyl cellulose, carbomer, and a mixture thereof.

5. The liquid preparation of claim 1, wherein the liquid preparation comprises the thickener at a concentration of about 0.5 mg/mL to about 100 mg/mL.

6. The liquid preparation of claim 1, wherein the buffer is one or more selected from the group consisting of a borate, a acetate, a carbonate, a citrate, a lactate, and a hydrate thereof.

7. The liquid preparation of claim 6, wherein the buffer is one or more selected from the group consisting of ammonium carbonate, sodium acetate, potassium acetate, calcium carbonate, calcium lactate, potassium citrate, sodium citrate, sodium bicarbonate, sodium lactate, and a hydrate thereof.

8. The liquid preparation of claim 6, wherein the buffer is a pharmaceutically acceptable salt of citric acid or a hydrate thereof.

9. The liquid preparation of claim 1, wherein the liquid preparation further comprises a solvent.

10. The liquid preparation of claim 1, wherein the liquid preparation is a syrup.

11. The liquid preparation of claim 3, wherein the liquid preparation further comprises a sweetener.

12. The liquid preparation of claim 11, wherein the sweetener is one selected from the group consisting of acesulfame potassium, aspartame, dextrate, dextrose, fructose, high fructose, galactose, maltose, mannitol, maltitol, xylitol, stevia, steviol glycoside, enzymatically modified stevia, saccharin, saccharin calcium, saccharin sodium, sorbitol, sorbitol solution, sucralose, sucrose, white sugar, syrup, simple syrup, honey, and a mixture thereof.

13. The liquid preparation of claim 1, wherein the liquid preparation further comprises an additive selected from the group consisting of a diluent, a solubilizing agent, a flavoring agent, a preservative, a sweetener, an acidifier, and a mixture thereof.

14. The liquid preparation of claim 13, wherein the preservative is one selected from the group consisting of benzoic acid, sodium benzoate, methyl paraoxybenzoate, ethyl paraoxybenzoate, propyl paraoxybenzoate, butyl paraoxybenzoate, sorbic acid, potassium sorbate, sodium sorbate, chlorobutanol, cresol, chlorocresol, and a mixture thereof.

15. A liquid preparation comprising:

L-serine or a pharmaceutically acceptable salt thereof in an amount of about 50 mg/mL to about 500 mg/mL;

one or more thickener selected from the group consisting of sodium carboxymethyl cellulose, povidone, hydroxyethyl cellulose, and carbomer;

a buffer; and a solvent, wherein the liquid preparation has a pH of 4.0 to 7.0, and wherein the liquid preparation is an oral preparation.

16. The liquid preparation of claim 15, wherein the liquid preparation further comprises one selected from the group consisting of a diluent, an acidifier, a preservative, a sweetener, and a mixture thereof.

17. A liquid preparation comprising:

L-serine or a pharmaceutically acceptable salt thereof in an amount of about 50 mg/mL to about 500 mg/mL;

a thickener selected from sodium carboxymethyl cellulose, povidone, or a mixture thereof;

a buffer, which is a salt of citric acid; and a solvent, which is one selected from the group consisting of water, purified water, water for injection, Ringer's solution, physiological saline, and a mixture thereof, wherein the liquid preparation has a pH of 4.0 to 7.0, and wherein the liquid preparation is an oral preparation.

18. The liquid preparation according to claim 1, wherein the liquid preparation is a solution.

19. A method for treating a central nervous system disease of a subject in need thereof, comprising administering to the subject an effective amount of the liquid preparation according to claim 1.

20. The method of claim 19, wherein the central nervous system disease is one or more selected from the group consisting of autism spectrum disorder, Alzheimer's disease, Parkinson's disease, intellectual disability, learning disability, language disorder, attention deficit hyperactivity disorder, emotional disorder, motor disorder, hypoxic-ischemic brain injury, traumatic brain injury, neuroinflammatory disease, cerebrovascular disease, attention disorder, and memory disorder.

21. The method of claim 19, wherein the central nervous system disease is autism spectrum disorder.

22. A method for preparing the liquid preparation according to claim 1, the method comprising:

(1) dissolving a thickener in a solvent to prepare a first solution;

(2) adding a pharmaceutically acceptable first additive to the first solution and heating the mixture to prepare a second solution having a pH of about 4.0 to about 7.0 at about 50° C. or greater, wherein the pharmaceutically acceptable first additive comprises a buffer; and (3) cooling the second solution, and then dissolving L-serine or a pharmaceutically acceptable salt thereof and a pharmaceutically acceptable second additive in the cooled second solution to prepare a third solution.

23. The method of claim 22, wherein the pharmaceutically acceptable first additive further comprises one or more selected from the group consisting of an acidifier, a solubilizing agent, and a preservative.

24. The method of claim 22, wherein the pharmaceutically acceptable second additive further comprises one or more selected from the group consisting of a diluent, a sweetener, a flavoring agent, and a coloring agent.

* * * * *